United States Patent

Miyazawa et al.

[11] 4,169,890
[45] Oct. 2, 1979

[54] PHARMACEUTICAL COMPOSITION CONTAINING 5″-AMINO-3′,5″-DIDEOXY-RIBOSTAMYCIN AND INTERMEDIATE COMPOUNDS

[75] Inventors: Takeo Miyazawa; Yukio Horiuchi, both of Yokohama; Eiichi Akita, Kamakura; Hamao Umezawa; Sumio Umezawa, both of Tokyo, all of Japan

[73] Assignee: Meiji Seika Kaisha, Ltd., Tokyo, Japan

[21] Appl. No.: 800,857

[22] Filed: May 26, 1977

Related U.S. Application Data

[63] Continuation-in-part of Ser. No. 696,834, Jun. 17, 1976, abandoned.

[30] Foreign Application Priority Data

Jun. 30, 1975 [JP] Japan .................................. 50-80094

[51] Int. Cl.$^2$ ....................... A61K 31/71; C07H 15/22
[52] U.S. Cl. ................................. 424/180; 536/17 R
[58] Field of Search ..................... 536/10, 17; 424/180

[56] References Cited

U.S. PATENT DOCUMENTS

| | | | |
|---|---|---|---|
| 3,784,541 | 1/1974 | Culbertson et al. | 536/17 |
| 3,923,783 | 12/1975 | Naito et al. | 536/17 |
| 3,929,761 | 12/1975 | Umezawa et al. | 536/10 |
| 3,929,762 | 12/1975 | Umezawa et al. | 536/17 |
| 3,940,382 | 2/1976 | Umezawa et al. | 536/17 |
| 4,065,616 | 12/1977 | Umezawa et al. | 536/17 |

*Primary Examiner*—Johnnie R. Brown
*Attorney, Agent, or Firm*—Frishauf, Holtz, Goodman & Woodward

[57] ABSTRACT

A process for preparing a novel antibiotic, 5″-amino-3′,5″-dideoxy-ribostamycin, which comprises subjecting a ribostamycin derivative represented by the formula:

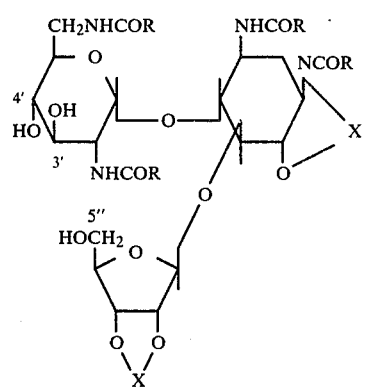

to selective sulfonylation to form a 3′,5″-O-disulfonyl derivative, subjecting the thus produced derivative to azide-forming reaction with sodium azide, subjecting the thus produced ribostamycin 3′-O-sulfonyl-5″-azido derivative to deoxylation by treating it with sodium borohydride in an aprotic and polar solvent, subjecting the thus obtained 3′ deoxy derivative to catalytic hydrogenation in the presence of a catalyst to form a 5″-amino derivative and then, removing the remaining protective groups of the last-mentioned derivative.

5 Claims, No Drawings

PHARMACEUTICAL COMPOSITION CONTAINING 5''-AMINO-3',5''-DIDEOXY-RIBOSTAMYCIN AND INTERMEDIATE COMPOUNDS

RELATED APPLICATION

This application is a continuation-in-part of our application Ser. No. 696,834, filed June 17, 1976, which has been abandoned.

This invention relates to 5''-amino-3',5''-dideoxyribostamycin, a novel compound represented by the formula (IV)

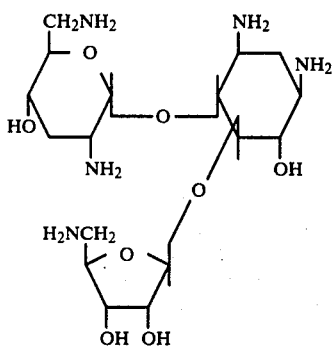

to a process for preparing the same, and to an antimicrobial composition containing the same.

An object of this invention is to provide a novel ribostamycin derivative namely, 5''-amino-3',5''-dideoxyribostamycin having the above formula (IV).

A further object of this invention is to provide a process for preparing the above-identified ribostamycin derivative (IV).

Another object of this invention is to provide a novel antimicrobial composition containing the above-mentioned ribostamycin derivative (IV), which shows an excellent antimicrobial activity, particularly against Psudomonas aeruginosa.

We have found that 5''-amino-3',5''-dideoxyribostamycin, a novel compound represented by the following formula (IV)

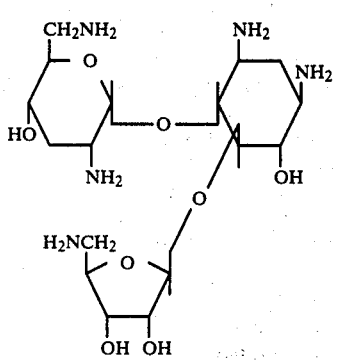

can be obtained by treating the 3'-O-sulfonyl-5''-azido derivative represented by the formula (III)

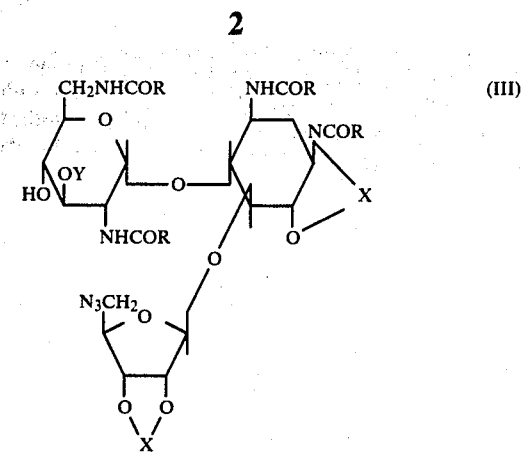

wherein R represents a known protective group for an amino group selected from an alkyloxy group, particularly an alkyloxy group having 1 to 4 carbon atoms, and an aryloxy group, and X represents a known protective group for a hydroxyl group selected from a group

(wherein P and P' are the same or different and each represents a hydrogen atom, an alkyl group having 1 to 2 carbon atoms or a phenyl group) and a cyclohexylidene group, and Y represents an alkylsulfonyl group, an aralkylsulfonyl group (particularly, benzylsulfonyl group) or an arylsulfonyl group, with sodium borohydride in an aprotic, polar solvent such as diglyme (diethylene glycol dimethyl ether) to epoxidize and 3'-deoxydize the said azido-derivative (methods for such treatment are disclosed in the specifications of Japanese Patent applications Nos. 49-141497/74 and 49-141498/74, now Publications Nos. 51-68541/76 and 51-68542/76, respectively; U.S. Ser. No. 638,045 now U.S. Pat. No. 4,078,138 corresponds to the latter), subjecting the resulting compound to catalytic hydrogenation in the presence of a hydrogenating catalyst such as palladium black or platinum black to aminate the azido group at the 5''-position and then removing the remaining protective groups by a conventional method or methods.

The 3'-O-sulfonyl-5''-azido derivative of the formula (III), which is also a novel compound, can be obtained by subjecting a derivative of the formula (I)

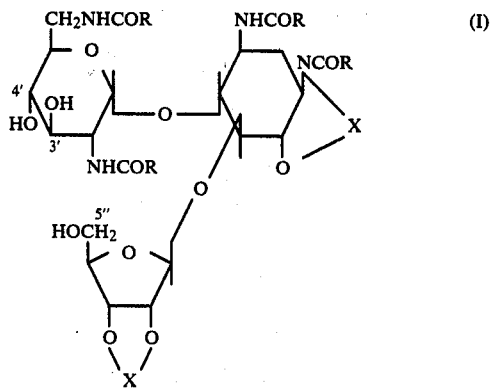

wherein R and X have the same meanings as above, to selective sulfonylation with an alkylsulfonyl chloride, an aralkylsulfonyl chloride or an arylsulfonyl chloride to form a 3′,5″-O-disulfonyl derivative represented by the formula (II)

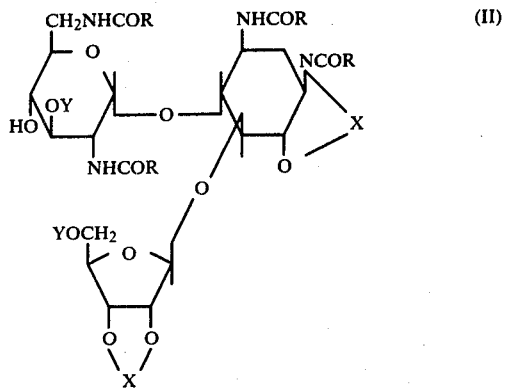

wherein R, X and Y have the same meanings as above, and further subjecting this derivative to an azide-forming reaction, whereby only the 5″-position is substituted with an azido group, by treating it with an azide-forming agent such as sodium azide, etc., and the derivative of the formula (III) can also be obtained by subjecting a derivative of the formula (I′)

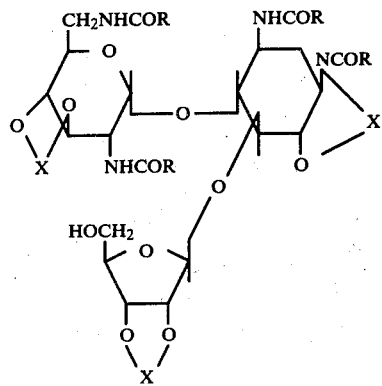

wherein R and X have the same meanings as above, to selective sulfonylation with an alkylsulfonyl chloride, an aralkylsulfonyl chloride or an arylsulfonyl chloride so as to form a 5″-O-sulfonyl derivative represented by the formula (II′)

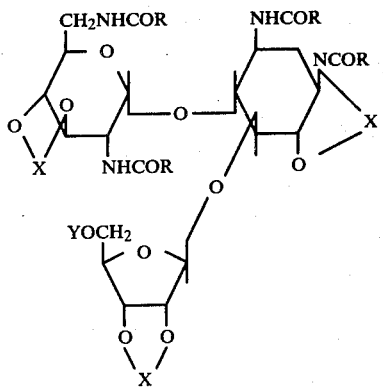

wherein R, X and Y have the same meanings as above, subjecting this derivative to an azide-forming reaction with sodium azide, whereby only the 5″-position is substituted with an azido group, by treating it with an azide-forming agent such as sodium azide, etc., subjecting the 5″-azido derivative represented by the formula (III′)

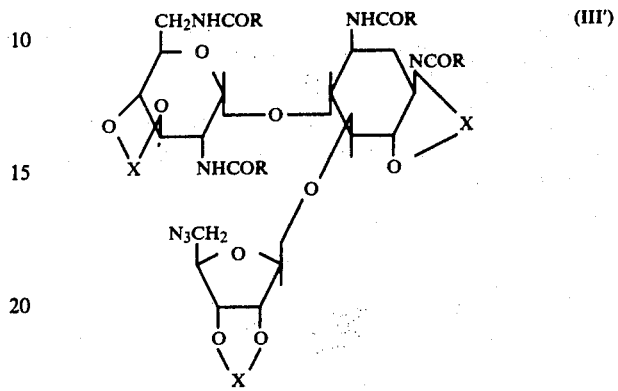

wherein R and X have the same meanings as above, to selectively remove the X group at the 3′-O- and 4′-O-positions, and further subjecting the resulting derivative to selective sulfonylation with an alkylsulfonyl chloride, an aralkylsulfonyl chloride or an arylsulfonyl chloride at the 3′-O-position.

The above-mentioned starting compounds derived from ribostamycin and represented by the above formula (I), in which the amino groups and hydroxyl groups of ribostamycin are protected by a known protective method, are publicly known (Annual Report of Meiji Seika Kaisha Ltd., No. 13, 1–20 (1973)). The compounds of the formula (I′) are novel.

As hereinbefore set forth, the present invention is directed to a process for preparing 5″-amino-3′,5″-dideoxyribostamycin, which principally comprises the following steps.

A 3′-O-sulfonyl-5″-azido derivative (III) is treated with sodium borohydride in an aprotic, polar solvent such as diglyme to be epoxidized and 3′-deoxydized; the resulting compound is catalytically hydrogenated in the presence of a hydrogenating catalyst to aminate the azido group at the 5″-position; and then, the remaining protective groups of the resulting product are removed.

In the above-stated process, each of the steps such as the treatment with sodium borohydride, the catalytic hydrogenation and the removal of the protective groups can be carried out in conventional ways. In other words, these reactions are well known to those skilled in the art, and hence there seems to be no need of describing these procedures in detail. Generally, however, the catalytic hydrogenation may be carried out by employing a hydrogen gas in the presence of a catalyst such as palladium black or platinum black, and the protective-group-removing reaction may be carried out by employing an appropriate acid or base.

The ribostamycin derivatives (III) which are the starting compounds of the above-stated process can be prepared by the aforementioned processes, that is, (I) → (II) → (III) and (I′) →(II′) →(III′) →(III).

In these processes, selective sulfonylation and azide-forming reactions are both involved. These reactions are likewise known to those skilled in the art, and there seems to be no need of describing these procedures in detail. Generally, however, the selective sulfonylation may be carried out by employing a known sulfonylating agent such as an alkylsulfonyl halide, an aralkylsulfonyl halide or an arylsulfonyl halide, e.g., p-toluenesulfonyl chloride, or by utilizing the method disclosed in Japanese Provisional Patent Publication No. 49-80038/74 (sulfonylation of 5''-hydroxyl group).

According to the specifications of Japanese Patent applications Nos. 49-87499, 49-141497 and 49-141498, a compound which contains a 3',4'-α-epoxy-Neamine group (Neamine itself of Neamine group contained in a molecule of an antibiotic is epoxidized at the 3'- and 4'-positions) and protected or unprotected groups can reportedly be reduced to the corresponding 3'-deoxy-compound by catalytic hydrogenation in a basic solvent in the presence of a skeleton catalyst, and to the corresponding 4'-deoxy-3'-epi compound by treating the compound with sodium borohydride.

Owing to the presence of an azido group at the 5''-position, the 3',4'-epoxy derivative of the present invention is reduced to the corresponding 4'-deoxy-3'-epi derivative by catalytic hydrogenation in a basic solvent in the presence of a skeleton catalyst and to the corresponding 3'-deoxy derivative by treating with sodium borohydride. The results differ remarkably from those of the method described in Japanese Patent applications No. 49-87499 and 49-141497. Namely, it should be noted that, in case where the 5'-hydroxyl group of ribostamycin is substituted by an azido group, the selectivity of the monoalcohol-forming reaction is entirely the reverse of that of the reaction of the 5''-hydroxy derivative.

The amination of the 5''-position of an antibiotic having a ribostamycin or xylostasin skeleton was carried out by T. H. Haskell et al in respect of Butirosin A and B (J. Antibiotics 26, 790 (1973)) or 4'-deoxybutirosin (Japanese Patent application No. 49-66130). However, 5''-amino-3',5''-dideoxyribostamycin of the present invention is a novel compound, in which the effect of the growth inhibition is enhanced in comparison with its original compound, ribostamycin, as shown in Table 1.

Table 1

Antimicrobial spectrum of 5''-amino-3',5''-dideoxyribostamycin

| Microorganism submitted to test | | Minimum Inhibition Concentration (mcg/ml) | |
|---|---|---|---|
| | | 5''-Amino-3',5''-dideoxy-ribostamycin | Ribostamycin (as compared) |
| Staphylococcus aureus | FDA 209P | 1.56 | 3.12 |
| Escherichia coli | K-12 | 6.25 | 3.12 |
| '' | ML - 1629 | 12.5 | > 100 |
| '' | ML - 1410 | 6.25 | 3.12 |
| '' | R-81 | 12.5 | > 100 |
| '' | R-56 | 6.25 | 3.12 |
| '' | JR66/W677 | 25 | > 100 |
| Pseudomonas aeruginosa | A3 | 6.25 | > 100 |
| '' | No. 12 | 25 | > 100 |
| '' | H-9 | 25 | > 100 |
| '' | TI-13 | 12.5 | > 100 |
| '' | H-11 | 25 | > 100 |
| Esherichia coli | K-12.J5R-11-12 | 6.25 | > 100 |
| Mycobacterium | 607 | 3.12 | 6.25 |

As is clear from the above table, 5''-amino-3',5''-dideoxy-ribostamycin has stronger antimicrobial activity, particularly against Pseudomonas aeruginosa, than that of ribostamycin.

According to test of acute toxicity with male mice (JCL-ICR) the toxicity of the present compound is $LD_{50}$ 200 mg/kg.

The present compound may form part of pharmaceutical compositions which are useful in the treatment of infectious diseases in human and veterinary practice.

Such compositions contain as an active component 5''-amino-3',5''-dideoxyribostamycin and/or salts thereof with non-toxic, pharmaceutically acceptable acids, together with solid or liquid pharmaceutical carriers and/or diluents.

In the said compositions, the proportion of therapeutically active material to carrier substance can very between 1% and 100% by weight. The compositions can be worked up to various pharmaceutical forms of presentation, such as tablets, pills, dragess, suppositories, capsules, sustained-release tablets, suspensions, injection medicines and the like containing 5''-amino-3',5''-dideoxyribostamycin or their atoxic salts, mixed with carriers and/or diluents.

Pharmaceutical organic or inorganic, solid or liquid carriers and/or diluents suitable for oral, enteral or parenteral administration can be used to make up compositions containing the present compound. Gelatine, lactose, starch, magnesium stearate, talc, vegetable and animal fats and oils, gum, polyalkylene glycol, buffers or other known carriers and/or diluents for medicaments are all suitable.

The preferred salt of the present compound is the hydrochloride, but salts with other inorganic or organic acids including antibiotically active acids may be used, e.g. the phosphate or the acetate. Furthermore, the compositions may contain other pharmaceutically active components which can appropriately be administered together with 5''-amino-3',5''-dideoxyribostamycin in the treatment of infectious diseases, such as other suitable antibiotics.

The present compound and salts thereof may be worked up to pharmaceutical forms of presentation including suspensions and non-aqueous ointments and creams. A pharmaceutical preparation for oral treatment may be in the form of a suspension of the present compound as such or in the form of a sparingly soluble salt with a pharmaceutically acceptable acid, the preparation containing from 20 to 100 mg per ml of a non-aqueous vehicle. A pharmaceutical preparation for topical treatment may be in the form of a non-aqueous ointment or cream containing the present compound in an amount of from ½ to 10g per 100g of preparation.

The compounds produced according to the invention shall be administered in such doses that the desired activity is achieved without simultaneous secondary effects. In human therapy, the compound and salts thereof are conveniently administered (to adults) in dosage units containing not less than 50mg and up to 1000mg, preferably from 250 to 750 mg, calculated as the compound of formula I.

By the term "dosage unit" is meant a unitary, i.e. a single dose which is capable of being administered to a patient, and which may be readily handled and packed, remaining as a physically stable unit dose comprising either the active material as such or a mixture or it with solid or liquid pharmaceutical diluents or carriers.

In the form of a dosage unit, the compound may be administered once or more times a day at appropriate intervals, always depending, however, on the condition of the patient, and in accordance with the prescription made by the medical practitioner.

Thus a daily dose will preferably be an amount of from 1 to 3 g of a compound of formula I.

If the composition is to be injected, a sealed ampoule, a vial or a similar container may be provided containing a parenterally acceptable aqueous or oily injectable solution or dispersion of the active material as the dosage unit.

The parenteral preparations are in particular useful in the treatment of conditions in which a quick response to the treatment is desirable. In the continuous therapy of patients suffering from infectious diseases, the tablets or capsules may be the appropriate form of pharmaceutical preparation owing to the prolonged effect obtained when the drug is given orally, in particular in the form of sustained-release tablets.

In the treatment of infectious diseases, such tablets may advantageously contain other active components, as mentioned hereinbefore.

The invention will be further described in the following Examples which are not to be construed as limiting the invention.

EXAMPLE 1.

Synthesis of 5''-amino-3',5''-dideoxyribostamycin 9 g of tetra-N-ethoxycarbonylribostamycin (See Japanese Patent Application No. 47-122436), which was prepared according to the method described in Japanese Provisional Patent Publication No. 49-80038, was dissolved in 90 ml of anhydrous DMF, and 460 mg of p-toluenesulfonic acid and 17.6 ml of 1,1-dimethoxycyclohexane were added thereto. The resulting mixture was stirred at 55° C. under reduced pressure. To the reaction mixture were added 380 mg of p-toluenesulfonic acid and 10 ml of 1,1-dimethoxy-cyclohexane at an interval of 1 hour. After addition thereof eight times, 40 g of sodium bicarbonate (NaHCO₃) was added and the mixture was concentrated to dryness. The residue was extracted with chloroform and the extract was evaporated to dryness after washing with water. Without isolating the product, the resulting residue was dissolved in 150 ml of a mixed solvent consisting of 40 %-acetic acid and acetone at a ratio of 1 : 4. After heating the mixture at 60° C. for 3 hours, NaHCO₃ was added in such an amount that the reaction mixture was made basic and acetone was removed by evaporation. The resulting mixture was extracted with chloroform, washed with water and evaporated to dryness. The residue was subjected to purification with a column of alumina (solvent, CHCl₃ : EtOH=40:1) to separate 8.48 g of 1,6-N,O-2'',3'':3',4'-O-tricyclohexylidene-1,2',3,6'-tetra-N-ethoxycarbonyl ribostamycin.

500 mg of the above tricyclohexylidene-derivative was subjected to reaction with 388 mg of p-toluenesulfonyl chloride in pyridine at room temperature to give the 5''-O-tosyl derivative, which was further subjected to reaction with 165 mg of sodium azide in DMF at 110° C. for 2 hours to give 370 mg of the 5''-azido derivative. The 5''-azido derivative was dissolved in 14 ml of a mixed solvent (80% -acetic acid : acetone − 1:1) and heated at 50° C. for 30 minutes. After reaction, the mixture was neutralized with NaHCO₃ and acetone was removed by evaporation. The resulting mixture was extracted with chloroform and the organic layer was evaporated to dryness to give 5''-azido-1,6-N,O-2'',3''-dicyclohexylidene-1,2',3,6'-tetra-N-ethoxycarbonyl-ribostamycin.

Further, the product was tosylated at the 3'-position with 470 mg of p-toluenesulfonyl chloride to obtain 320 mg of the 5''-azido-3'-O-tosyl derivative. After the 5''-azido-3'-O-tosyl derivative was subjected to reaction with 78 mg of sodium borohydride in diglyme at 60° C. for 3 hours, water was added to the reaction mixture to form a precipitate. The product was further subjected to catalytic hydrogenation in methanol in the presence of Pd-black as a catalyst to give the 5''-aminated derivative. The remaining cyclohexylidene groups or ethoxycarbonyl groups were removed by treating with an acid or a base respectively to give 5''-amino-3',5''-dideoxyribostamycin. After purification with Amberlite CG-50 (NH₄⁺-type), 25.1 mg of the pure product was separated. The yield of product based on ribostamycin was 11.0%. $[\alpha]_D = +52.2°$ (C 1.0, H₂O), m.p. 119–121° C. (decomp.), Mass spectrometry (N-Ac, O-TMS derivative) m/e =835

Example 2 Synthesis of
5''-amino-3',5''-dideoxyribostamycin

According to the method in Example 1., 7.4 g of tetra-N-ethoxycarbonyl ribostamycin was subjected to reaction to form the cyclohexylidene derivative. The product was dissolved in 120 ml of a mixed solvent (80%-acetic acid : acetone = 1:1) and heated at 60° C. for 1.5 hours. After concentration to dryness, the residue was extracted with chloroform. The organic layer was washed with a saturated solution of NaHCO₃ and then with water, and concentrated to dryness to give 8.72 g of crude 1,6-N,O-2 α,3''-O-dicyclohexylidene-1,2',3,6'-tetra-N-ethoxycarbonylribostamycin.

1.78 g of the dicyclohexylidene-derivative was subjected to reaction with 3.0 g of p-toluenesulfonyl chloride in pyridine at 50° C. to give 2.13 g of 1,6-N,O-2'',3''-O-dicyclohexylidene-1,2'',3,6'-tetra-N-ethoxy carbonyl-3',5''-di-O-tosylribostamycin. 312 mg of the ditosyl derivative was subjected to reaction with 117 mg of sodium azide in DMF at 100° C. for 2 hours to give the 5''-azido-3'-O-tosyl derivative, which was further subjected to reaction with 49 mg of sodium borohydride in diglyme at 60° C. for 3 hours to give the 3'-deoxy derivative. According to the procedure in Example 1., the amination, removing of the protective groups and purification were successively carried out to obtain 16 mg of 5''-amino-3',5''-dideoxyribostamycin. The yield based on ribostamycin was 7.8%.

Referential Example Synthesis of
5''-amino-4',5''-dideoxy-3'-epi-ribostamycin 680 mg of 5''-azido-1,6-N,O-2'',3''-O-dicyclohexylidene-1,2',3,6'-tetra-N-ethoxycarbonyl-3'-O-tosylribostamycin, which was obtained according to the method described in Example 1. or Example 2., was dissolved in 13.6 ml of 2.8% solution of sodium methoxide. After adding 10 cc of Raney nickel, catalytic hydrogenation was conducted at room temperature under ordinary pressure. After removing the Raney nickel by filtration the resulting mixture was concentrated. After removing the cyclohexylidene groups and ethoxycarbonyl groups, the product was purified tp give 65 mg of 5''-amino-4',5''-dideoxy-3'-epi-ribostamycin. Yield: 10.0%. $[\alpha]_D = +30.2°$ (C 1.0, H₂O) m.p. 125–126° C.

The corresponding Japanese Provisional Patent Publications of the Japanese Patent Applications mentioned in the present specification are as follows:

| Japanese Pat. Appln. No. | (mentioned at) | Japanese Provisional Pat. Publn. No. |
|---|---|---|
| 49-87499 | (page 8, line 19) | 51-16642/76 |
| 49-66130 | (page 9, line 15) | 50-35132/75 |
| 47-122436 | (page 13, lines 24–25) | 49-80038/74 |

As the skeleton catalyst mentioned at page 8, line 25 and at page 9, line 3 may be mentioned Raney nickel catalyst which is prepared by treating an aluminum-nickel alloy with alkali and is usually employed as a catalyst for hydrogenation.

As the catalyst used for the hydrogenation of 3'-deoxy-5"-azido derivative of the present invention to form the 5"-amino derivative, there may be mentioned, for example, palladium black and platinum black.

As the alkylsulfonyl halide and aralkylsulfonyl halide mentioned at page 8, lines 13–14 in the present specification, there may be mentioned, for example, methanesulfonyl chloride, ethanesulfonyl chloride and benzylsulfonyl chloride.

What we claim is:

1. A compound represented by the formula (III)

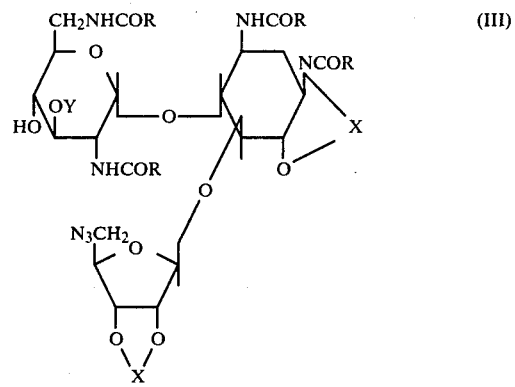

wherein R represents alkoxy having from 1 to 4 carbon atoms and X represents cyclohexylidene or

wherein P and P' are the same or different and each represents hydrogen, alkyl having 1 to 2 carbon atoms or phenyl, and Y represents alkylsulfonyl, benzylsulfonyl or p-toluenesulfonyl.

2. A compound of claim 1, wherein X represents cyclohexylidene.

3. 5"-Azido-1,6-N,O-2",3"-dicyclohexylidene-1,2',3,6'-tetra-N-ethoxycarbonyl-5"-deoxyribostamycin of the formula of claim 1.

4. 5"-Azido-1,6-N,O-2",3"-dicyclohexylidene-3'-O-tosyl-1,2',3,6'-tetra-N-ethoxycarbonyl-5"-deoxyribostamycin of the formula of claim 1.

5. An antimicrobial composition conatining as an active ingredient 5"-amino-3',5"-dideoxyribostamycin or a salt thereof with hydrochloric acid, phosphoric acid or acetic acid in association with a pharmaceutically acceptable carrier.

* * * * *